United States Patent [19]

Kreider

[11] 4,076,717
[45] Feb. 28, 1978

[54] DERIVATIVES OF 1-(3-CYANO-3,3-DIPHENYLPROPYL)-4-PHENYLPIPERIDINE-4-CARBOXYLIC ACID

[75] Inventor: Eunice M. Kreider, Chicago, Ill.

[73] Assignee: G. D. Searle & Co., Chicago, Ill.

[21] Appl. No.: 490,765

[22] Filed: Jul. 22, 1974

Related U.S. Application Data

[62] Division of Ser. No. 208,445, Dec. 15, 1971, Pat. No. 3,843,646.

[51] Int. Cl.$^2$ .......................................... C07D 211/06
[52] U.S. Cl. .................................................. 260/293.75
[58] Field of Search .................................... 260/293.75

[56] References Cited

U.S. PATENT DOCUMENTS 3,539,579  11/1970  Janssen ........................... 260/293.75

Primary Examiner—Paul J. Killos
Attorney, Agent, or Firm—John J. McDonnell

[57] ABSTRACT

The subject compounds are ester, thioester, amide, hydrazide and anhydride derivatives of 1-(3-cyano-3,3-diphenylpropyl)-4-phenylpiperidine-4-carboxylic acid. These compounds are prepared by reacting the aforementioned acid with the appropriate alcohol, thiol, amine, or the like in the presence of a suitable dehydrating agent, or by reacting the acid chloride derivative of the aforementioned acid with the appropriate alcohol, thiol, amine or the like. A further embodiment of this invention is N-oxide derivative of 1-(3-cyano-3,3-diphenylpropyl)-4-phenylpiperidine-4-carboxylic acid. This N-oxide compound is prepared by peracid treatment of the mentioned acid. The instant compounds share various valuable pharmacological properties, including analgesic and especially potent antidiarrheal properties.

4 Claims, No Drawings

DERIVATIVES OF 1-(3-CYANO-3,3-DIPHENYLPROPYL)-4-PHENYL-PIPERIDINE-4-CARBOXYLIC ACID

This is a division of application Ser. No. 208,445, filed 12/15/71 now U.S. Pat. No. 3,843,646.

The present invention relates to novel compounds characterized by the general structural formula

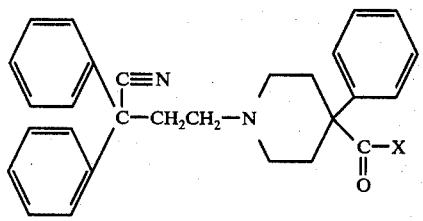
(I)

wherein X is an aryloxy or heteroaryloxy radical; a radical of the formula —NHNRR$_1$ wherein R and R$_1$, which can be the same or different, are each a hydrogen atom or an alkyl, aryl, alkanoyl or toluenesulfonyl radical, and in addition, when R is hydrogen R$_1$ can also be a 1-(3-cyano-3,3-diphenylpropyl)-4-phenylpiperidine-4-carbonyl radical, or R and R$_1$ can be combined to represent a radical of the formula

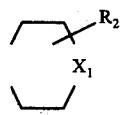

wherein X$_1$ is sulfur, oxygen, —NH— or —(CH$_2$)$_n$— wherein n is 0, 1 or 2, and R$_2$ represents hydrogen or one or more methyl substituents; X can further be a radical of the formula

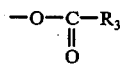

wherein R$_3$ is an alkyl, aryl, trifluoromethyl or 1-(3-cyano-3,3-diphenylpropy)-4-phenylpiperidine-4-carbonyloxy radical; X can further be a radical of the formula —SX$_2$ wherein X$_2$ is a hydrogen atom or an alkyl, aralkyl, heteroaralkyl, aryl or heteroaryl radical; X can further be a radical of the formula —NR$_4$R$_5$ wherein R$_4$ and R$_5$, which can be the same or different, are each an alkoxyalkyl, cycloalkyl, aryl or heteroaryl radical, R$_4$ can additionally be hydrogen, or R$_4$ and R$_5$ can be combined so that the radical —NR$_4$R$_5$ represents a succinimido, glutarimido, phthalimido or maleimido radical; or X is a radical of the formula X$_3$-alkylene-Y wherein X$_3$ is oxygen, sulfur or —NH—, and wherein Y is a radical of the formula —NR$_6$R$_7$ wherein R$_6$ and R$_7$, which can be the same or different, are each an alkyl or aralkyl radical, or R$_6$ and R$_7$ are combined so that the radical —NR$_6$R$_7$ represents a succinimido, glutarimido, phthalimido or maleimido radical; Y can further be a radical of the formula

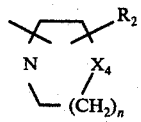

wherein R$_2$ and n are defined as before and X$_4$ is oxygen, sulfur, —NH— or —CH$_2$—; Y can further be a radical of the formula

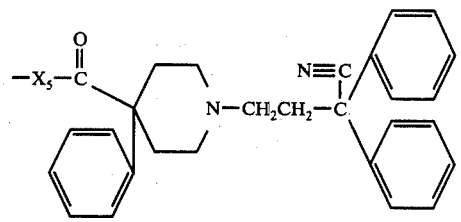

wherein x$_5$ is oxygen, sulfur or —NH—; or Y can be a cyano, alkanoyl, aroyl, heteroaroyl, carbalkoxy or heteroaryl radical; and, in addition, when X$_3$ is —NH—, Y can also be an aryl radical.

The term "aryl" used here and throughout this specification encompasses unsubstituted aryl radicals such as phenyl and naphthyl and also the corresponding aryl radicals containing one or more substituents, which may be the same or different, such as alkylthio, alkyl, halo, alkoxy, nitro, alkanoyl, carbalkoxy, dialkylamino, alkanoyloxy, trifluoromethyl, alkylsulfonyl and cyano groups. Similarly, the term "heteroaryl" used here and throughout this specification encompasses unsubstituted radicals such as pyridine, quinoline, isoquinoline pyrimidine and pyrazine, as well as the corresponding radicals containing one or more methyl groups. In addition, here and throughout this specification, the following definitions are applicable: The alkyl radicals contain 1 to 7 carbon atoms, e.g. methy, ethyl, propyl, butyl, pentyl, hexyl and heptyl and the branched-chain isomers thereof. The cycloalkyl radicals contain 5 to 7 carbon atoms, i.e. cyclopentyl, cyclohexyl, cycloheptyl. The alkylene moieties contain 1 to 6 carbon atoms and can be straight or branched-chain, e.g. methylene, ethylene, propylene, trimethylene, 1,2-butylene, 2,3-butylene, tetramethylene and the like. The aryloxy and heteroaryloxy radicals can be represented by the formula -O-aryl  and  -O-heteroaryl, respectively, wherein aryl and heteroaryl are defined as before. The alkoxy and alkanoyl radicals are of the type -O-alkyl  and

respectively, wherein alkyl is as hereinabove defined. The aralkyl, heteroaralkyl and alkoxyalkyl radicals possess the formulas -alkylene-aryl, -alkylene-heteroaryl, and alkylene-O-alkyl respectively, wherein alkylene, aryl, heteroaryl and alkyl have the meanings given above. The aroyl and heteroaroyl radicals can be represented by the formulas

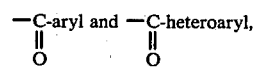

respectively, wherein aryl and heteroaryl are defined as before. The carbalkoxy, alkylthio, dialkylamino, alkanoyloxy and alkylsulfonyl radicals are of the type

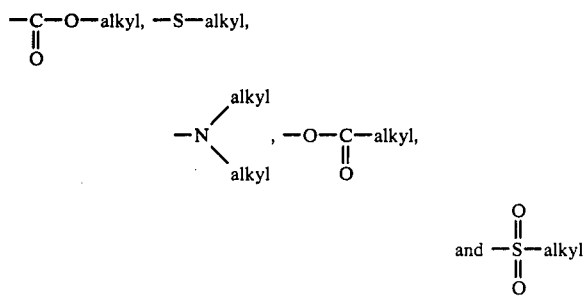

respectively, wherein alkyl is as hereinabove defined.

A further embodiment of this invention is an N-oxide derivative of 1-(3-cyano-3,3-diphenylpropyl)-4-phenylpiperidine-4-carboxylic acid. This oxido compound can be prepared by treatment of the corresponding basic substance with a peracid such as peracetic acid or m-chloroperbenzoic acid suitably in the presence of chloroform. As an alternative, the acid starting material may be used in its equivalent metallic salt form.

The compounds of formula (I) can be conveniently prepared by contacting a compound of the general formula

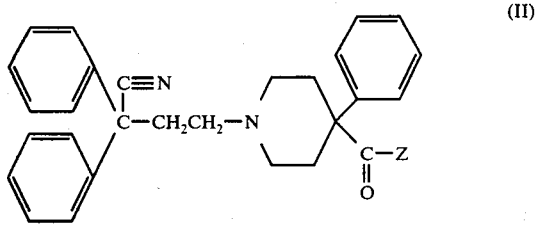

(II)

wherein Z is a chlorine atom or a hydroxy radical, with a compound of the formula

X—H       (III)

wherein X is defined as before.

When Z in formula (II) is a hydroxy radical, i.e. when the acid starting material is employed, the reaction is conducted in the presence of a suitable dehydrating agent. Suitable dehydrating agents include aromatic carbodiimides such as diphenylcarbodiimide; and aliphatic carbodiimides such as diethylcarbodiimide and, preferably, dicyclohexylcarbodiimide. Other dehydrating agents which may be suitable include bases such as sodium carbonate and acids such as sulfuic acid, hydrochloric acid and toluenesulfonic acid. Other possible dehydrating agents include trifluoroacetic anhydride and boron trifluoride etherate. Time, temperature and pressure are not critical factors for the conduct of this reaction; however, the reaction is preferably conducted initially at slightly elevated temperature, e.g. between 40°–60° C., and conveniently at atmospheric pressure. Typical reaction times vary between 3 hours and 3 days and are dependent on the particular temperature and reactants involved. Suitable solvents are non-protic solvents (i.e. solvents containing no acidic hydrogen atoms) which are capable of dissolving the acid of formula (II) at the temperature employed. Such suitable solvents include dimethylformamide, dimethylacetamide, and hexamethylphosphoramide.

When Z in formula (II) is a chlorine atom, i.e. when the starting material is the acid chloride, the reaction is conveniently conducted in the presence of a suitable base. Preferred bases for use in this reaction include tertiary aliphatic or aromatic amines, e.g. N-methylmorpholine, triethylamine, pyridine and picoline. The reaction is conveniently carried out at atmospheric pressure, at a temperature ranging from room temperature to reflux and for a time period of 5 minutes to 24 hours. However, time, temperature and pressure are not critical factors in conducting the reaction. Suitable solvents are non-protic solvents, e.g. dimethylformamide, dimethylacetamide, hexamethylphosphoramide, dimethylsulfoxide, tetrahydrofuran, acetonitrile, benzene and the like.

The starting material of formula (II) wherein Z is a chlorine atom is conveniently prepared from the corresponding acid of formula (II) by reaction with thionyl chloride in an inert solvent such as tetrahydrofuran, optionally in the presence of dimethylformamide. The acid chloride of formula (II) is particularly useful in the form of its hydrohalide salts, especially in the form of its hydrochloride. Of the starting materials represented by formula (II), the acid chloride is also the starting material of choice when X in the compound of formula (III) is —NHNH$_2$. The acid chloride of formula (II) in the form of its acid addition salts, especially in the form of its hydrochloride, is also valuable in view of the antidiarrheal activity which it shares with the compounds of formula (I).

The compounds of formula (I) wherein X is a radical of the formula -O-alkylene-Y wherein Y is defined as before can also be prepared by a highly desirable alternate route which utilizes the compound of formula (II) wherein Z is a hydroxy radical as a starting material. That acid is contacted with a compound of the formula Hal-alkylene-Y wherein Y is defined as before and Hal is a halogen atom, preferably a chlorine or bromine atom, to afford the corresponding compound of formula (I). The reaction is conveniently conducted in the presence of a suitable base, preferred bases including tertiary aliphatic or aromatic amines, e.g. N-methylmorpholine, triethylamine, pyridine and picoline. Time, temperature and pressure are not critical factors for the conduct of this reaction; however, the reaction is conveniently carried out at atmospheric pressure, at a temperature ranging from room temperature to slightly below the boiling point of the particular base employed, and for a time period ranging from about 3 hours to 3 days. Suitable solvents are non-protic solvents which are capable of dissolving the acid of formula (II) at the temperature employed. Such suitable solvents include dimethylformamide, dimethylacetamide, and hexamethylphosphoramide.

An alternate route to the subject compound wherein X is a radical of the formula —NHNH$_2$ involves contacting an alkyl ester of the acid of formula (II), preferably the ethyl ester, with lithium hydrazide.

Another route to the compounds of formula (I) wherein X is a radical of the formula

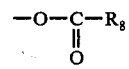

wherein R$_8$ is an alkyl, aryl or trifluoromethyl radical consists of reacting the acid starting material of formula (II) with an anhydride of the formula

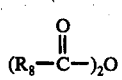

wherein $R_8$ is defined as above.

Equivalent to the free bases of formula (I) for the purposes of this invention are the non-toxic pharmaceutically acceptable acid addition salts thereof. Such salts include those derived from inorganic acids such as hydrochloric, hydrobromic, hydriodic, sulfuric, phosphoric, nitric, and sulfamic; and from organic acids such as acetic, citric, lactic, maleic, malic, succinic, tartaric, cinnamic, benzoic, gluconic, ascorbic, salicylic, ethane disulfonic, fumaric, glycolic, and related acids.

The compounds of the present invention possess valuable pharmacological properties. They are, for example, potent antidiarrheal agents. They are also capable of counteracting the withdrawal symptoms of certain substances which produce drug addiction and, in this regard, present advantage over the acid precursor of formula II and its corresponding ethyl ester. Additionally, the compounds of this invention variously possess analgesic, anti-protozoal, anti-bacterial, anti-algal, anti-fungal and anthelmintic activity.

The antidiarrheal properties of the instant compounds are specifically illustrated by the activity of the representative species 3-pyridyl 1-(3-cyano-3,3-diphenylpropyl)-4-phenylpiperidine-4-carboxylate dihydrochloride in the following test procedures.

Charcoal Meal Test

Mice weighing 18–24 grams and previously fasted for 18 hours were each given orally 0.3 ml. of a suspension containing 10% charcoal and 5% acacia. The test compounds were administered intragastrically one hour prior to the charcoal meal. One-half hour after administration of the meal the mice were sacrificed with ether and their gastrointestinal tracts were removed. The distance over which some of the charcoal meal had moved from the pylorus to the cecum was measured for each mouse and expressed as percentage of the total distance. Each compound was tested at three dose levels (typically, at 0.3, 0.6 and 1.2 mg/mouse) in groups of 5 mice per dose level. Control groups of mice given saline only were run concurrently with each test group.

Castor Oil-Induced Diarrhea Test

Male Charles River rats were fasted overnight and water given ad lib. Test compounds (0.1 mg./kg.) were administered orally in normal saline, while controls were given saline only. The rats were randomized into two treatment groups and one control group, each group containing 10 rats. One hour after compound administration, 1 ml. of castor oil was given to each rat intragastrically. The rats were then observed for the presence or absence of diarrhea one hour after administration of the castor oil.

For the treatment of diarrhea, the novel compounds of this invention can be combined with pharmaceutically acceptable carriers to provide novel pharmaceutical compositions. The concentration of active ingredient in the composition is not critical, but is preferably 1–80%. These compounds can be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose or cellulose acetate phthalate; gelatin; talc; calcium phosphates such as dicalcium phosphate or tricalcium phospate; sodium sulfate; calcium sulfate; polyvinyl pyrrolidone, acacia; polyvinyl alcohol; stearic acid; alkaline earth metal stearates such as magnesium stearate; oils such as peanut oil, cottonseed oil, sesame oil, olive oil, corn oil, oil of theobroma; water; agar; alginic acid; and benzyl alcohol, as well as other nontoxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard, for which the therapeutic dosage is known.

The invention will appear more fully from the following Examples, which are set forth for the purpose of illustration only.

EXAMPLE 1

To 7 grams of 1-(3-cyano-3,3-diphenylpropyl)-4-phenylpiperidine-4-carboxylic acid suspended in 100 ml. of anhydrous tetrahydrofuran and 5 ml. of redistilled N,N-dimethylformamide was added 8 ml. of thionyl chloride in 50 ml. of anhydrous tetrahydrofuran. The resulting clear solution was stirred at room temperature under anhydrous conditions for about 5 minutes, then heated at the reflux temperature for 15 minutes and concentrated to dryness. To the residue was added an equal volume of tetrahydrofuran and the resultant mixture was contacted with a stream of nitrogen and stripped of solvent by vacuum distillation. The residue was triturated with cold tetrahydrofuran, then filtered. The filtrate was concentrated to dryness at room temperature in a nitrogen atmosphere. The solid residue was filtered with anhydrous ether and dried at room temperature in vacuo, thus affording 1-(3-cyano-3,3-diphenylpropyl)-4-phenylpiperidine-4-carboxylic acid chloride hydrochloride, melting at about 169°–171° C. with decomposition.

EXAMPLE 2

2.12 Grams of 1-(3-cyano-3,3-diphenylpropyl)-4-phenylpiperidine-4-carboxylic acid was dissolved in 65 ml. of redistilled N,N-dimethylformamide together with 0.50 gram of 2-hydroxypyridine by warming to approximately 80° C. The solution was cooled to about 50° C. and 1.16 grams of dicyclohexylcarbodiimide was added. The resultant mixture was stirred at room temperature under anhydrous conditions for 48 hours, then cooled to approximately 5° C. The precipitate which formed was removed by filtration and the filtrate was diluted with 100 ml. of aqueous 5% sodium chloride solution and extracted three times with 100 ml. portions of ethyl acetate. The combined ethyl acetate solutions were washed three times with water; then dried over anhydrous sodium sulfate and concentrated to approximately one-half the original volume to afford a precipitate which, upon recrystallization from a mixture of tetrahydrofuran and isopropyl ether, gave the ureide formed by the reaction of dicyclohexylcarbodiimide with 1-(3-cyano-3,3-diphenylpropyl)-4-phenylpiperidine-4-carboxylic acid, melting at about 170°–172° C. The ethyl acetate filtrate was acidified with concentrated hydrochloric acid in 2-propanol, diluted with isopropyl ether and cooled to give a precipitate which was washed with ethyl ether and dried in vacuo at about 65° C. There was thus obtained 2-pyridyl 1-(3-cyano-3,3-diphenylpropyl)-4-phenylpiperidine-4-carboxylate dihydrochloride, melting at about 201°–205° C.

EXAMPLE 3

2.12 Grams of 1-(3-cyano-3,3-diphenylpropyl)-4-phenylpiperidine-4-carboxylic acid was dissolved in 60 ml. of warm redistilled N,N-dimethylformamide. To that solution was then added 0.48 gram of 3-hydroxypyridine, followed by 1.16 grams of dicyclohexylcarbodiimide. The resultant solution was stirred at room temperature under anhydrous conditions for about 24 hours, a precipitate appearing after approximately 1 hour. The suspension was cooled to about 5° C., the precipitate was removed by filtration, and the filtrate was diluted with 100 ml. of water and extracted twice with 100 ml. portions of ethyl acetate. The combined ethyl acetate layers were washed with water, dried over anhydrous sodium sulfate, concentrated to approximately one-half volume by evaporation under a stream of nitrogen, and then filtered. The ethyl acetate solution was acidified with concentrated hydrochloric acid in 2-propanol, diluted with ethyl ether and cooled. The precipitate which formed was recrystallized from a mixture of N,N-dimethylformamide and isopropyl ether containing decolorizing carbon, then dried in vacuo at about 65° C. There was thus obtained 3-pyridyl 1-(3-cyano-3,3-diphenylpropyl)-4-phenylpiperidine-4-carboxylate dihydrochloride, melting at about 208.5°–211° C. with gas evolution.

Substitution of 0.55 gram of 2-pyridinemethanol for the 3-hydroxypyridine used above and substantial repetition of the foregoing procedure afforded, after acidification with concentrated hydrochloric acid in 2-propanol, a solution which was diluted with ethyl ether and cooled. The precipitate which formed was recrystallized from a mixture of 2-propanol, isopropyl ether and N,N-dimethylformamide containing decolorizing charcoal and dried. The product was 2-pyridylmethyl 1-(3-cyano-3,3-diphenylpropyl)-4-phenylpiperidine-4-carboxylate dihydrochloride hydrate, melting at about 146°–149° C.

Similarly, substitution of 0.83 gram of N-benzyl-N-methylethanolamine for the 3-hydroxypyridine used above and substantial repetition of the procedure detailed in the first paragraph of this Example afforded, after acidification with concentrated hydrochloric acid in 2-propanol, a solution which was diluted with ethyl ether and cooled. The precipitate which formed was recrystallized from a mixture of isopropyl ether and 2-propanol containing decolorizing carbon and dried, thus affording 2-(N-benzyl-N-methylaminoethyl) 1-(3-cyano-3,3-diphenylpropyl-4-phenylpiperidine-4-carboxylate dihydrochloride, compound with 2-propanol.

When 4.24 grams of 1-(3-cyano-3,3-diphenylpropyl)-4-phenylpiperidine-4-carboxylic acid was dissolved in 120 ml. of warm redistilled N,N-dimethylformamide, 1.16 grams of dicyclohexylcarbodiimide was added and the procedure described in the first paragraph of this Example was substantially repeated, there was obtained 1-(3-cyano-3,3-diphenylpropyl)-4-phenylpiperidine-4-carboxylic acid anhydride.

EXAMPLE 4

1.20 Grams of 1-(3-cyano-3,3-diphenylpropyl)-4-phenylpropyl)-4-phenylpiperidine-4-carboxylic acid was dissolved in 55 ml. of warm redistilled N,N-dimethylformamide. To the resultant solution was then added 0.56 gram of 2,4,5-trichlorophenol, followed by 0.60 grams of dicyclohexylcarbodiimide. The reaction mixture was stirred at room temperature under anhydrous conditions for about 24 hours, a precipitate appearing after approximately 1 hour. The suspension was cooled to about 5° C. The precipitate was removed by filtration and the filtrate was diluted with 100 ml. of water and extracted twice with 100 ml. portions of ethyl acetate. The combined ethyl acetate layers were washed with water, dried over anhydrous sodium sulfate, concentrated to approximately one-half volume by evaporation under a stream of nitrogen, and then filtered. The ethyl acetate solution was then acidified with concentrated hydrochloric acid in 2-propanol, diluted with ethyl ether and cooled. The precipitate which formed was dried at about 80° C. There was thus obtained 2,4,5-trichlorophenyl 1-(3-cyano-3,3-diphenylpropyl)-4-phenylpiperidine-4-carboxylate hydrochloride, melting at 221°–222° C.

EXAMPLE 5

3.36 Grams of 1-(3-cyano-3,3-diphenylpropyl)-4-phenylpiperidine-4-carboxylic acid was dissolved in 140 ml. of warm redistilled N,N-dimethylformamide. To that solution was then added 1.22 grams of 3-methyl-(4-methylthio)phenol, followed by 1.75 grams of dicyclohexylcarbodiimide. The resultant solution was stirred at room temperature under anhydrous conditions for about 24 hours, a precipitate appearing after approximately 1 hour. The suspension was cooled to about 5° C., the precipitate was removed by filtration, and the filtrate was diluted with water and extracted with ethyl acetate. The ethyl acetate extract was washed with water, dried over anhydrous potassium carbonate, concentrated to approximately one-half volume by evaporation under a stream of nitrogen, and then filtered. The ethyl acetate solution was then acidified with concentrated hydrochloric acid in 2-propanol, diluted with ethyl ether, and cooled. The precipitate which formed was recrystallized from a mixture of methyl ethyl ketone and hexane, then dried to afford 3-methyl-(4-methylthio)phenyl 1-(3-cyano-3,3-diphenylpropyl)-4-phenylpiperidine-4-carboxylate hydrochloride, melting at about 217°–219° C.

EXAMPLE 6

3.36 Grams of 1-(3-cyano-3,3-diphenylpropyl)-4-phenylpiperidine-4-carboxylic acid was dissolved in 100 ml. of warm redistilled N,N-dimethylformamide. To that solution was then added 0.23 gram of ethylene glycol, followed by 1.60 grams of dicyclohexylcarbodiimide. The resultant solution was stirred at room temperature under anhydrous conditions for about 21 hours, then cooled. The precipitate which formed was removed by filtration and the filtrate was diluted with water and extracted with ethyl acetate. The ethyl acetate solution was washed with water, dried over anhydrous potassium carbonate and filtered. The ethyl acetate solution was then acidified with concentrated hydrochloric acid in 2-propanol, diluted with ethyl ether, and cooled. The oil obtained was neutralized with aqueous sodium bicarbonate, reextracted with ethyl acetate, washed with water, and dried. That ethyl acetate solution was then acidified with concentrated hydrochloric acid in 2-propanol, diluted with hexane and cooled. The precipitate which formed was recrystallized from a mixture of 2-propanol and isopropyl ether containing decolorizing carbon. There was thus obtained ethylene bis-1 1-(3-cyano-3,3-diphenylpropyl)-4-phenylpiperidine-4-carboxylate)1 dihydrochloride, compound with 2-propanol, foaming at about 170° C.

EXAMPLE 7

3.18 Grams of 1-(3-cyano-3,3-diphenylpropyl)-4-phenylpiperidine-4-carboxylic acid was dissolved in 80 ml. of warm redistilled N,N-dimethylformamide. To that solution was then added, while cooling in an ice bath, 1.30 grams of 2,4-dichlorothiophenol, followed by 1.60 grams of dicyclohexylcarbodiimide. The resultant solution was stirred and allowed to warm to room temperature over a 24 hour period under anhydrous conditions, then cooled to about 5° C. The precipitate which formed was removed by filtration, and the filtrate was diluted with water and extracted with ethyl acetate. The ethyl acetate solution was washed with water, dried over anhydrous sodium sulfate, concentrated to approximately one-half volume by evaporation under a stream of nitrogen, and then filtered. The ethyl acetate solution was then acidified with concentrated hydrochloric acid in 2-propanol, diluted with ethyl ether, cooled, filtered and dried. The precipitate was recrystallized from a mixture of methanol and ethyl ether and dried in vacuo at about 65° C., affording S-(2,4-dichlorophenyl) 1-(3-cyano-3,3-diphenylpropyl)-4-phenylpiperidine-4-thiocarboxylate hydrochloride. That product melted at about 219°–222° C.

EXAMPLE 8

2.12 Grams of 1-(3-cyano-3,3-diphenylpropyl)-4-phenylpiperidine-4-carboxylic acid was dissolved in 65 ml. of warm redistilled N,N-dimethylformamide. To that solution was then added 0.62 gram of benzyl mercaptan, followed by 1.16 grams of dicyclohexylcarbodiimide. The resultant solution was stirred at room temperature under anhydrous conditions for approximately 48 hours, then cooled and filtered. The filtrate was diluted with water and extracted with ethyl acetate. The ethyl acetate solution was washed with water, dried over anhydrous potassium carbonate, concentrated to approximately one-half volume, acidified with concentrated hydrochloric acid in 2-propanol, diluted with hexane and cooled. The precipitate which formed was recrystallized from a mixture of 2-propanol and isopropyl ether, thus affording S-benzyl 1-(3-cyano-3,3-diphenylpropyl)-4-phenylpiperidine-4-thiocarboxylate hydrochloride, melting at about 180°–182° C.

Substitution of 0.56 gram of furfuryl mercaptan for the benzyl mercaptan used above and substantial repetition of the foregoing procedure afforded, after acidification with concentrated hydrochloric acid in 2-propanol, a solution which was diluted with isopropyl ether and cooled. The precipitate which formed was recrystallized from a mixture of ethyl acetate and hexane, thus affording S-furfuryl 1-(3-cyano-3,3-diphenylpropyl)-4-phenylpiperidine-4-thiocarboxylate hydrochloride. That product melted at about 180°–182° C. with decomposition.

EXAMPLE 9

2.12 Grams of 1-(3-cyano-3,3-diphenylpropyl)-4-phenylpiperidine-4-carboxylic acid was suspended in 20 ml. of dry tetrahydrofuran containing 1 ml. of redistilled N,N-dimethylformamide. To that suspension was added 3.5 ml. of thionyl chloride in 8 ml. of dry tetrahydrofuran. The resultant solution was stirred for approximately 10 minutes at room temperature, then refluxed for 20 minutes and concentrated to dryness. To the residue was added 10 ml. of dry tetrahydrofuran, and the solution was stripped of solvent by vacuum distillation. An additional 10 ml. of dry tetrahydrofuran was added and the solution was again stripped of solvent by vacuum distillation. The solid residue thus obtained was dissolved in 15 ml. of redistilled N,N-dimethylformamide by warming. To that solution was added 0.48 gram of 4-picoline, followed by 2.0 grams of N-(2-hydroxyethyl)morpholine in 5 ml. of trichloromethane. The resultant solution was stirred for about 15 minutes, then diluted with 50 ml. of water and extracted twice with 50 ml. portions of ethyl acetate. The combined ethyl acetate extracts were washed with water, dried, acidified with concentrated hydrochloric acid in 2-propanol and then diluted with ethyl ether to the point of incipient precipitation. The precipitate which formed was recrystallized, first from a mixture of methanol and ethyl ether containing decolorizing carbon, and then from a mixture of tetrahydrofuran and hexane, thus affording 2-morpholinoethyl 1-(3-cyano-3,3-diphenylpropyl)-4-phenylpiperidine-4-carboxylate dihydrochloride, melting at about 198°–200° C. with gas evolution.

Substitution of an equivalent quantity of 3-hydroxypyridine for the N-(2-hydroxyethyl)morpholine used above and substantial repetition of the foregoing procedure afforded, after acidification with concentrated hydrochloric acid in 2-propanol, a solution which was diluted with ethyl ether and cooled. The precipitate which formed was recrystallized from a mixture of N,N-dimethylformamide and isopropyl ether containing decolorizing charcoal, then dried in vacuo at about 65° C. There was thus obtained 3-pyridyl 1-(3-cyano-3,3-diphenylpropyl)-4-phenylpiperidine-4-carboxylate dihydrochloride, melting at about 208.5°–211° C. with gas evolution.

EXAMPLE 10

2.12 Grams of 1-(3-cyano-3,3-diphenylpropyl)-4-phenylpiperidine-4-carboxylic acid was dissolved in 60 ml. of redistilled N,N-dimethylformamide by warming to approximately 60° C. To the resultant solution was added 1.25 grams of N-bromomethylphthalimide, followed by 0.55 gram of triethylamine in 5 ml. of redistilled N,N-dimethylformamide. The solution was stirred at room temperature under anhydrous conditions for about 24 hours, then diluted with 100 ml. of water and extracted twice with 100 ml. portions of ethyl acetate. The combined ethyl acetate extracts were washed with water dried over anhydrous potassium carbonate, acidified with concentrated hydrochloric acid in 2-propanol, and diluted with ethyl ether. Upon cooling, a precipitate formed which was recrystallized from a mixture of methyl ethyl ketone, methanol, and hexane containing decolorizing carbon, then dried in vacuo at about 65° C., thus affording phthalimidomethyl 1-(3-cyano-3,3-diphenylpropyl)-4-phenylpiperidine-4-carboxylate hydrochloride, melting at about 230°-232° C.

Substitution of 0.94 gram of ethyl 2-bromopropionate for the N-bromomethylphthalimide used above and substantial repetition of the foregoing procedure afforded, after acidification with concentrated hydrochloric acid in 2-propanol, crude 1-carbethoxyethyl 1-(3-cyano-3,3-diphenylpropyl)-4-phenylpiperidine-4-carboxylate hydrochloride.

EXAMPLE 11

2.12 Grams of 1-(3-cyano-3,3-diphenylpropyl)-4-phenylpiperidine-4-carboxylic acid was dissolved in 60 ml. of redistilled N,N-dimethylformamide by warming to approximately 60° C. To the resultant solution was added .4 gram of chloracetonitrile, followed by .55 gram of triethylamine. The solution was stirred at room temperature under anhydrous conditions for about 24 hours, then diluted with water and extracted with ethyl acetate. The ethyl acetate extract was washed with water, acidified with concentrated hydrochloric acid in 2-propanol, diluted with ethyl ether and cooled. The precipitate which formed was recrystallized from a mixture of methanol and tetrahydrofuran, affording cyanomethyl 1-(3-cyano-3,3-diphenylpropyl)-4-phenylpiperidine-4-carboxylate hydrochloride, melting at about 243.5°-245.5° C.

EXAMPLE 12

2.12 Grams of 1-(3-cyano-3,3-diphenylpropyl)-4-phenylpiperidine-4-carboxylic acid was dissolved in 65 ml. of redistilled N,N-dimethylformamide by warming to approximately 60° C. To the resultant solution was added 1.17 grams of α-bromo-4-chloroacetophenone, followed by 0.55 gram of triethylamine in 5 ml. of redistilled N,N-dimethylformamide. The solution was stirred at room temperature under anhydrous conditions for approximately 48 hours, the diluted with water and extracted with ethyl acetate. The ethyl acetate extract was washed with water, dried over anhydrous sodium sulfate, concentrated to about one-half volume, acidified with concentrated hydrochloric acid in 2-propanol, diluted with ethyl ether, and cooled. The precipitate which formed was recrystallized from a mixture of methanol and tetrahydrofuran containing decolorizing carbon, thus affording 4-chlorophenacyl 1-(3-cyano-3,3-diphenylpropyl)-4-phenylpiperidine-4-carboxylate hydrochloride, melting at about 235°-238° C.

EXAMPLE 13

2.12 Grams of 1-(3-cyano-3,3-diphenylpropyl)-4-phenylpiperidine-4-carboxylic acid was dissolved in 65 ml. of warm redistilled N,N-dimethylformamide. To that solution was then added 0.30 gram of 1,1-dimethylhydrazine, followed by 1.16 grams of dicyclohexylcarbodiimide. The resultant solution was stirred at room temperature under anhydrous conditions for about 24 hours, then cooled. The precipitate which formed was removed by filtration and the filtrate was diluted with water and extracted with ethyl acetate. The ethyl acetate solution was washed with water, dried over anhydrous sodium sulfate, concentrated to approximately one-half volume and then filtered. The ethyl acetate solution was then acidified with concentrated hydrochloric acid in 2-propanol, diluted with ethyl ether and cooled. The precipitate which formed was twice recrystallized from a mixture of 2-propanol and isopropyl ether. There was thus obtained 1-[1-(3-cyano-3,3-diphenylpropyl)-4-phenylpiperidine-4-carbonyl]-2,2-dimethylhydrazine dihydrochloride, compound with 2-propanol. That product softened about 175° C. and foamed at approximately 190° C.

Substitution of .65 gram of N-(2-aminoethyl)morpholine for the 1,1-dimethylhydrazine used above and substantial repetition of the foregoing procedure afforded N-(2-morpholinoethyl)-1-(3-cyano-3,3-diphenylpropyl)-4-phenylpiperidine-4-carboxamide dihydrochloride, compound with 2-propanol, foaming at approximately 165° C.

Similarly, substitution of 0.69 gram of 4-methoxybenzylamine for the 1,1-dimethylhydrazine used above and substantial repetition of the procedure detailed in the first paragraph of this Example afforded N-(4-methoxybenzyl)-1-(3-cyano-3,3-diphenylpropyl)-4-phenylpiperidine-4-carboxamide hydrochloride, melting at about 201°-204° C.

In like manner, substitution of 0.64 gram of 4-chloroaniline for the 1,1-dimethylhydrazine employed in the first paragraph of this Example and substantial repetition of the procedure described therein afforded, after acidification with concentrated hydrochloric acid in 2-propanol, a solution which was diluted with ethyl ether and cooled. The precipitate which formed was recrystallized from a mixture of isopropyl ether, 2-propanol and N,N-dimethylformamide, thus affording N-(4-chlorophenyl)-1-(3-cyano-3,3-diphenylpropyl)-4-phenylpiperidine-4-carboxamide hydrochloride, melting at about 231°-235° C.

EXAMPLE 14

A mixture of 2.12 grams of 1-(3-cyano-3,3-diphenylpropyl)-4-phenylpiperidine-4-carboxylic acid and 15 ml. of trifluoroacetic acid anhydride was refluxed under anhydrous conditions for approximately 48 hours. Excess trifluoroacetic acid anhydride was removed by vacuum distillation and to the solid residue thus obtained was added dioxane. The resultant mixture was filtered and the filtrate was diluted with ethyl ether. The crude product thus obtained was the trifluoroacetic acid salt of the anhydride of 1-(3-cyano-3,3-diphenylpropyl)-4-phenylpiperidine-4-carboxylic acid with trifluoroacetic acid.

EXAMPLE 15

When equivalent quantities of acethydrazide, N-aminomorpholine and 1,1-diphenylhydrazine were substituted for the 3-hydroxypyridine employed in the first paragraph of Example 3 and the procedure described therein was substantially repeated there were obtained the hydrochloride salts of 1-[1-(3-cyano-3,3-diphenylpropyl)-4-phenylpiperidine-4-carbonyl]-2-acetylhydrazine; N-morpholino-1-(3-cyano-3,3-diphenylpropyl)-4-phenylpiperidine-4-carboxamide; and 1-[1-(3-cyano-3,3-diphenylpropyl)-4-phenylpiperidine-4-carbonyl]-2,2-diphenylhydrazine, respectively.

Similarly, substitution of an equivalent quantity of α-hydroxy-4-chloroacetophenone for the 3-hydroxypyridine used in the first paragraph of Example 3 and substantial repetition of the procedure there detailed afforded, after acidification with concentrated hydrochloric acid in 2-propanol, a solution which was diluted with ethyl ether and cooled. The precipitate which formed was recrystallized from a mixture of methanol and tetrahydrofuran containing decolorizing carbon, thus affording 4-chlorophenacyl 1-(3-cyano-3, 3-diphenylpropyl)-4-phenylpiperidine-4-carboxylate hydrochloride, melting at about 235°–238° C.

In a similar manner, when an equivalent quantity of ethyl 2-hydroxypropionate was substituted for the 3-hydroxypyridine used in the first paragraph of Example 3 and the procedure described therein was substantially repeated, there was obtained, after acidification with concentrated hydrochloric acid in 2-propanol, crude 1-carbethoxyethyl 1-(3-cyano-3,3-diphenylpropyl)-4-phenylpiperidine-4-carboxylate hydrochloride.

In like manner, substitution of an equivalent quantity of N-hydroxymethylphthalimide for the 3-hydroxypyridine used in the first paragraph of Example 3 and substantial repetition of the procedure there detailed afforded, after acidification with concentrated hydrochloric acid in 2-propanol, a solution which was diluted with ethyl ether and cooled. The precipitate which formed was recrystallized from a mixture of methyl ethyl ketone, methanol and hexane containing decolorizing carbon, then dried in vacuo at about 65° C. There was thus obtained phthalimidomethyl 1-(3-cyano-3,3-diphenylpropyl)-4-phenylpiperidine-4-carboxylate hydrochloride, melting at about 230°–232° C.

Similarly, when an equivalent quantity of hydroxyacetonitrile was substituted for the 3-hydroxypyridine used in the first paragraph of Example 3 and the procedure described therein was substantially repeated, there was obtained, after acidification with concentrated hydrochloric acid in 2-propanol, a solution which was diluted with ethyl ether and cooled. The precipitate which formed was recrystallized from a mixture of methanol and tetrahydrofuran, affording cyanomethyl 1-(3-cyano-3,3-diphenylpropyl-4-phenylpiperidine-4-carboxylate hydrochloride melting at about 243.5°–245.5° C.

EXAMPLE 16

200 Mg. of a representative compound, e.g. 3-pyridyl 1-(3-cyano-3,3-diphenylpropyl)-4-phenylpiperidine-4-carboxylate dihydrochloride, was dissolved in 165 ml. of alcohol. To the resultant solution was added 450 ml. of glycerin. The mixture was stripped thoroughly while 1.0 ml. of cherry flavor and sufficient sorbitol solution to bring the total volume to 1000 ml. were added. The pH was adjusted to 8.5 to 9.0 using sodium or potassium hydroxide solution and the liquid was filtered. There was thus obtained a liquid having a concentration of active ingredient of 1 mg./5cc.

When the above procedure was repeating using 500 mg. of the active ingredient, 175 ml. of alcohol, 450 ml. of glycerin, 1.5 ml. of cherry flavor and sufficient sorbitol solution to bring the total volume to 1000 ml., there was obtained a liquid having a concentration of active ingredient of 2.5 mg./5cc.

EXAMPLE 17

2.5 Grams of a representative compound, e.g. 3-pyridyl 1-(3-cyano-3,3-diphenylpropyl)-4-phenylpiperidine-4-carboxylate dihydrochloride, was mixed with 37.19 grams of powdered sucrose and 22.05 grams of corn starch, then screened and remixed. The mixture was granulated with 0.63 gram of polyvinylpyrrolidone in ethanol, then dried and screened. 0.63 Gram of magnesium stearate was added and the product was remixed and compressed into tablets of the appropriate size. There was thus obtained a batch of 1000 tablets having a concentration of active ingredient of 2.5 mg./tablet.

When the above procedure was repeated using 1 gram of the active ingredient, 38.69 grams of powdered sucrose, 22.05 grams of corn starch, 0.63 gram of polyvinylpyrrolidone and 0.63 gram of magnesium stearate, there was obtained a batch of 1000 tablets having a concentration of active ingredient of 1.0 mg./tablet.

When the procedure of the first paragraph of this Example was repeated utilizing 2.5 grams of the active ingredient premixed with 25 mg. of atropine sulfate, 37.165 grams of powdered sucrose, 22.05 grams of corn starch, 0.63 gram of polyvinylpyrrolidone and 0.63 gram of magnesium stearate, there was obtained a batch of 1000 tablets having a concentration of 2.5 mg. of active ingredient and 0.025 mg. of atropine sulfate per tablet.

EXAMPLE 18

1.0 Gram of a representative compound, e.g. 3-pyridyl 1-(3-cyano-3,3-diphenylpropyl)4-phenylpiperidine-4-4-carboxylate dihydrochloride, and 249 grams of corn starch were mixed, screened, remixed and filled into No. 2 hard gelatin capsules by hand or machine using 250 mg. fill per capsule. There was thus obtained a batch of 1000 capsules having a concentration of active ingredient of 1.0 mg./capsule.

Repetition of the above precedure using 2.5 grams of the active ingredient and 247.5 grams of corn starch afforded a batch of 1000 capsules having a concentration of active ingredient of 2.5 mg./capsule.

EXAMPLE 19

6.3 Grams of 1-(3-cyano-3,3-diphenylpropyl)-4-phenylpiperidine-4-carboxylic acid was dissolved, at room temperature, in 100 ml. of glacial acetic acid. To that mixture was added 3.1 grams of m-chloroperbenzoic acid (85% by weight) and the resultant mixture was stirred at room temperature for a period of 1½ hours, thereafter diluted with 500 ml. of water, cooled and filtered. The residual solid was washed successively with water chloroform, ether and warm methanol. Upon drying for 6 hours at 65° C. was afforded 1-(3-cyano-3,3-diphenylpropyl)-4-phenyl-N-oxidopiperidine-4-carboxylic acid, melting at about 186°–189° C., with decomposition.

What is claimed is:
1. A compound of the formula

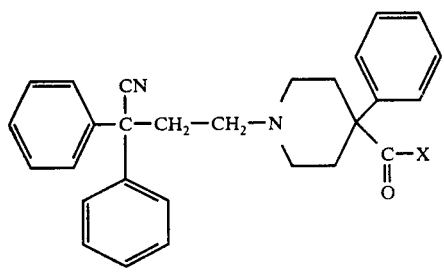

and the non-toxic pharmaceutically acceptable acid addition salts thereof, wherein X is 2-pyridylmethyloxy, 4-chlorophenylcarboxy, and 3-methyl-(4-methylthio)-phenyloxy.

2. The compound of claim 1 which is 3-methyl(4-methylthio)phenyl-1-(3-cyano-3,3-diphenylpropyl)-4-phenylpiperidine-4-carboxylate hydrochloride.

3. The compound of claim 1 which is 4-chlorophenacyl 1-(3-cyano-3,3-diphenylpropyl)-4-phenylpiperidine-4-carboxylate hydrochloride.

4. A compound according to claim 1 which is 2-Pyridylmethyl 1-(3-cyano-3,3-diphenylpropyl)-4-phenylpiperidine-4-carboxylate.

* * * * *